United States Patent [19]
Alby, III

[11] Patent Number: 6,121,203
[45] Date of Patent: Sep. 19, 2000

[54] METHOD FOR THE CONTROL OF GOATGRASSES

[75] Inventor: Theodore Alby, III, Vancouver, Wash.

[73] Assignee: American Cyanamid Company, Madison, N.J.

[21] Appl. No.: 09/222,142

[22] Filed: Dec. 29, 1998

Related U.S. Application Data

[60] Provisional application No. 60/070,243, Dec. 30, 1997.
[51] Int. Cl.$^7$ ..................................................... A01N 43/48
[52] U.S. Cl. ............................................................ 504/253
[58] Field of Search ..................................... 504/116, 253

[56] References Cited

U.S. PATENT DOCUMENTS

| | | | |
|---|---|---|---|
| 4,798,619 | 1/1989 | Los | 71/66 |
| 4,936,902 | 6/1990 | Walls, Jr. | 71/92 |
| 5,334,576 | 8/1994 | Doehner et al. | 504/128 |
| 5,773,704 | 6/1998 | Croughan | 800/235 |

OTHER PUBLICATIONS

Seedfeldt et al, Production of herbicide–resistant jointed goatgrass, Weed Sci., 46 (6), 632–634, 1998.

Fernald, Merritt Lyndon. Gray's Manual of Botany. Portland, OR: Dioscorides Pr. P. 136. Date: 1993.

Donald, William W., et al. "Biology and Control of Jointed Goatgrass (Aegilops Cylindrical), a Review". Wee Technology. 5:3–17. Date: 1991.

Anderson, Wood Powell. "Imidazolinone Herbicides", chpater 20 in Weed Science: Principles and Applications. 3$^{rd}$ ed. Minneapolis/St. Paul: West Publ. Co. pp. 200–201. Date: 1996.

*Primary Examiner*—Jose' G. Dees
*Assistant Examiner*—Alton Pryor
*Attorney, Agent, or Firm*—John W. Hogan, Jr.

[57] ABSTRACT

There is provided a method for the control of an Aegylops plant which comprises applying to said plant or the locus in which it is growing or to be grown a herbicidally effective amount of 2-(4-isopropyl-4-methyl-5-oxo-2-imidazolin-2-yl)-5-(methoxymethyl)nicotinic acid ("imazamox") or a salt thereof.

11 Claims, No Drawings

METHOD FOR THE CONTROL OF GOATGRASSES

This application claims the benefit of Provisional Appln. 60/070,243 filed Dec. 30, 1997.

BACKGROUND OF THE INVENTION

For centuries, cereal crops have supplied the means for sustaining life. Cereal crop production plays a crucial role in maintaining a viable economy in the predominantly agricultural regions of the world. Cereal crops include wheat, rice, barley, sorghum and the like. Grass weeds pose a particular problem in cereal crop production in that many herbicidal agents which control grass weeds also cause injury to the target crop species due to the similarity of the weed and crop monocotyledenous plant species. An especially difficult weed plant in cereal crop production is the Aegylops genus (goatgrasses) such as Aegylops cylindrica Host., Aegylops triuncialis L. Barb., Aegylops ovata L. and the like. This plant genus is physiologically and genetically similar to wheat and is difficult to control without concomitant injury to the wheat crop. The presence of goatgrass in wheat production can cause up to 30% yield reduction and contaminate the harvested crop, thus reducing its milling quality and potential use as seed for future crop production.

To date, the known methods to avoid or control the presence of goatgrass in cereal production is to plant alternative crops or allow the fields to lie fallow for some period of time. However, these methods are time-consuming, costly and not always practicable.

Imidazolinone herbicidal agents such as those described in U.S. Pat. No. 4,798,619 and U.S. Pat. No. 5,334,576 are known to be effective over a broad spectrum of broadleaf and grass weed species. These patents describe compounds having the structure:

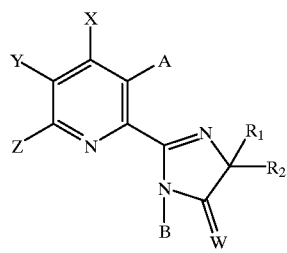

wherein A, B, $R_1$, $R_2$, W, X, Y and Z represent a wide variety of substituents. Said patents further describe the preemergence and postemergence herbicidal activity of more than a thousand of such pyridine and quinoline imidazolinones. U.S. Pat. No. 5,334,576 specifically discloses the compound 2-(4-isopropyl-4-methyl-5-oxo-2-imidazolin-2-yl)-5-(methoxymethyl)nicotinic acid and the herbicidal activity thereof against a wide variety of broadleaf and grass weed species. However, U.S. Pat. No. 4,798,619 and U.S. Pat. No. 5,334,576 do not disclose that 2-(2-imidazolin-2-yl) pyridines and quinolines are active against Aegylops weed species either alone or in the presence of a cereal crop.

SUMMARY OF THE INVENTION

The present invention relates to a method for the control of an Aegylops plant which comprises applying to the foliage of said plant or to the soil or water containing the seeds of said plant a herbicidally effective amount of 2-(4-isopropyl-4-methyl-5-oxo-2-imidazolin-2-yl)-5-(methoxymethyl)nicotinic acid ("imazamox") or a salt thereof.

The present invention further provides the selective control of an Aegylops plant in the presence of a cereal crop, particularly an imidazolinone-resistant or imidazolinone-tolerant cereal crop.

DETAILED DESCRIPTION OF THE INVENTION

Heretofore, there has been no feasible chemical control of Aegylops plant species (goatgrasses) such as Aegylops cylindrica (jointed goatgrass), Aegylops triuncialis, Aegylops ovata and the like, particularly Aegylops cylindrica. Surprisingly, it has now been discovered the one imidazolinone out of the one thousand or more imidazinones disclosed in U.S. Pat. No. 4,798,619 and U.S. Pat. No. 5,334,576; namely the compound 2-(4-isopropyl-4-methyl-5-oxo-2-imidazolin-2-yl)-5-(methoxymethyl)nicotinic acid, hereinafter referred to as imazamox, is unique in its ability to control Aegylops plant species. Advantageously, imazamox, or a salt thereof, may be used to control goatgrasses in the presence of a cereal crop such as wheat, rice, barley, sorghum, oat, corn and the like, particularly a Winter crop such as wheat, preferably imidazolinone-resistant wheat or imidazolinone-tolerant wheat. The control of goatgrass weed species establishes imazamox and its salts as unique among imidazolinones. The control of goatgrass weed species is especially useful in the presence of cereal crop plants, particularly small grain cereal crop plants, especially wheat plants.

Imazamox and a preparation therefor are described in U.S. Pat. No. 5,334,576. The chemical structure of imazamox is shown below as formula I.

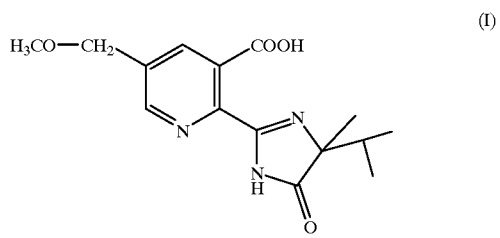

(I)

Salts of imazamox include all agriculturally acceptable salts such as alkali metal salts, alkaline earth metal salts, ammonium salts, organic ammonium salts and inorganic metal salts such as those described in U.S. Pat. No. 5,334,576. Preferable salts are ammonium salts or organic ammonium salts such as isopropylammonium.

The method of the invention is particularly useful for controlling goatgrasses, especially jointed goatgrass, in the presence of cereal crops such as wheat, rice, barley, sorghum, oat, corn and the like, particularly wheat. Preferred cereal crops are those crops which are imidazolinone resistant or imidazolinone tolerant such as IMI® wheat, IMI® corn and the like, preferably IMI® wheat.

In actual practice, imazamox or a salt thereof may be applied as a spray, dust, granule or the like or may be formulated as an aqueous concentrate solution, a water dispersible granular, a microencapsulated emulsion, a wettable powder, and the like, preferably an aqueous concentrate solution. Imazamox is sold under the trademark RAPTOR® herbicide by American Cyanamid Company.

The herbicidally effective amount of imazamox will vary according to the prevailing conditions such as weed population density, time of application, mode of application, weather conditions, topographical conditions and the like. In general, imazamox or a salt thereof may be applied to the foliage of the goatgrass or to the soil or water containing seeds of the goatgrass, preferably to the foliage, at rates of about 0.010 kg/ha to about 1.0 kg/ha, preferably at about 0.02 kg/ha to 0.08 kg/ha.

It is, of course, clear that rates of application in excess of the effective amount required to control the goatgrass may be used, however, rates of application of a herbicidal agent above that which is required for effective weed control should be avoided since excessive application rates are costly and serve no useful environmental or ecological function.

In order to facilitate a further understanding of the invention, the following examples are presented primarily for the purpose of illustrating certain more specific details thereof. The invention is not to be deemed limited thereby except as defined in the claims.

EXAMPLE 1

Field Trial Postemergence Evaluations Of Herbicidal Activity Of Imazamox

In these evaluations, small field plots in a variety of widespread geographical locations known to have dense populations of *Aegylops cylindrica* (jointed goatgrass) are used. The average plot size is approximately 3.5×9.5 meters and the plots are treated in a modified randomized complete block design with 3 to 4 replications. Soil types are predominantly silty loam soil. All treatments are applied using standard accepted weed science practices. All treatments include 0.25% v/v of a nonionic surfactant and about 1.25% v/v of a 10-0-0 liquid nitrogen fertilizer. An aqueous concentrate formulation (1 AS) of imazamox, such as that described in U.S. Pat. No. 4,816,060, is used. Crops are planted in the Fall and test applications are made the following Spring when the IMI® wheat crop is in the 2–3 leaf stage. Evaluations are made 59–71 days after treatment and recorded as % weed control as compared to an untreated check plot. In these tests, no injury to the IMI® wheat is observed. The data obtained are shown in Table I below. The data shown for each field trial is the mean value of said trial.

TABLE I

Postemergence Herbicidal Evaluation Of Imazamox On Jointed Goatgrass In The Presence Of IMI® Wheat

| Rate (kg/ha) | % Weed Control | | | | |
| --- | --- | --- | --- | --- | --- |
| | Trial I | Trial II | Trial III | Trial IV | Average |
| 0.0264 | 91 | 83 | 69 | 83 | 81 |
| 0.0352 | 97 | 85 | 83 | 100 | 88 |
| 0.0440 | 96 | 93 | 85 | — | 91 |
| 0.0528 | 100 | 91 | 86 | — | 92 |
| 0.0704 | 100 | 98 | 90 | — | 96 |

I claim:

1. A method for the control of an Aegylops plant which comprises applying to the foliage of said plant or to the soil or water containing the seeds of said plant a herbicidally effective amount of imazamox or a salt thereof.

2. The method according to claim 1 wherein the Aegylops plant is selected from the group consisting of *Aegylops cylindrica, Aegylops triuncialis* and *Aegylops ovata.*

3. The method according to claim 2 wherein the plant is *Aegylops cylindrica.*

4. The method according to claim 1 wherein the imazamox is applied in the presence of a cereal crop.

5. The method according to claim 4 wherein the cereal crop is selected from the group consisting of wheat, rice, barley, rye, sorghum, oat and corn.

6. The method according to claim 5 wherein the cereal crop is an imidazolinone-resistant or an imidazolinone-tolerant crop.

7. The method according to claim 6 wherein the crop is wheat.

8. The method according to claim 1 wherein the imazamox is applied at a rate of about 0.01 kg/ha to 1.0 kg/ha.

9. The method according to claim 8 wherein the rate is about 0.02 kg/ha to 0.08 kg/ha.

10. The method according to claim 1 wherein the imazamox is applied to the foliage of an Aegylops plant.

11. The method according to claim 10 wherein the imazamox is applied in the presence of a cereal crop.

* * * * *